US012560583B2

(12) United States Patent
O'Donncha et al.

(10) Patent No.: US 12,560,583 B2
(45) Date of Patent: Feb. 24, 2026

(54) QUANTIFICATION OF OCEANIC CARBON DIOXIDE SEQUESTRATION

(71) Applicant: INTERNATIONAL BUSINESS MACHINES CORPORATION, Armonk, NY (US)

(72) Inventors: Fearghal O'Donncha, Aran Islands (IE); Andrew James Stanford-Clark, Chale (GB); Adam James Thompson, Ruderting (DE); Ricardo Martinho, Lisbon (PT); Moritz Johannes Stäbler, Cologne (DE); Jonathan Wright, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 434 days.

(21) Appl. No.: 18/162,078

(22) Filed: Jan. 31, 2023

(65) Prior Publication Data

US 2024/0255481 A1     Aug. 1, 2024

(51) Int. Cl.
*G01N 33/00* (2006.01)

(52) U.S. Cl.
CPC ....... *G01N 33/004* (2013.01); *G01N 33/0063* (2013.01)

(58) Field of Classification Search
CPC ... G01N 33/004; G01N 33/0063; G01V 20/00
See application file for complete search history.

(56) References Cited

U.S. PATENT DOCUMENTS

| | | | |
|---|---|---|---|
| 2020/0398959 A1 | 12/2020 | Pomerantz | |
| 2021/0129078 A1 | 5/2021 | Regan | |
| 2023/0364554 A1* | 11/2023 | Romaniello | C02F 1/20 |
| 2024/0061977 A1* | 2/2024 | Ling | G01V 20/00 |
| 2024/0354851 A1* | 10/2024 | Stolt | G06Q 50/02 |

FOREIGN PATENT DOCUMENTS

WO        2021260732 A1    12/2021

OTHER PUBLICATIONS

Adornato et al., "In situ nutrient sensors for ocean observing systems", ResearchGate, https://www.researchgate.net/publication/254768909, Jan. 2009, pp. 1-11.

(Continued)

*Primary Examiner* — Mohammad K Islam
(74) *Attorney, Agent, or Firm* — Gavin Giraud

(57)        ABSTRACT

A method for quantifying oceanic carbon dioxide ($CO_2$) sequestration is provided. The method includes obtaining a plurality of oceanic spatiotemporal carbon dioxide ($CO_2$) measurements. A plurality of spatiotemporal chlorophyll a (Chl-a) and a plurality of oceanic temperature measurements are obtained. The obtained plurality of oceanic spatiotemporal $CO_2$ measurements is mapped to the obtained plurality of spatiotemporal Chl-a and the plurality of oceanic temperature measurements in a multidimensional grid. At least one a priori oceanic spatiotemporal $CO_2$ estimate is generated based on the multidimensional grid.

18 Claims, 2 Drawing Sheets

(56)     References Cited

OTHER PUBLICATIONS

Data Marine, "Copernicus Marine Data Store", https://data.marine. copernicus.eu/products, accessed Nov. 29, 2022, pp. 1-3.

Deseglise et al., "FAST-Infra Platform", https://www. climatepolicyinitiative.org/fast-infra-platform/, accessed Nov. 29, 2022, p. 1-5.

Elgin, Ben, "This Timber Company Sold Millions of Dollars of Useless Carbon Offsets", Mar. 17, 2022, https://www.bloomberg. com/news/articles/2022-03-17/timber-ceo-wants-to-reform-flawed-carbon-offset-market?leadSource=uverify%20wall, pp. 1-10.

Friedrich et al., "Neural network-based estimates of North Atlantic surface $pCO_2$ from satellite data: A Methodological Study", Journal of Geophysics, vol. 114, C03020, 2009, doi:10.1029/2007JC004646, pp. 1-12.

Gabrieli et al., "A Reconfigurable Integrated Electronic Tongue and its use in Accelerated Analysis of Juices and Wines", arXiv:2205. 15018v1 [cs.LG], May 27, 2022, pp. 1-3.

Gambin et al., "Sustainable Marine Ecosystems: Deep Learning for Water Quality Assessment and Forecasting", IEEE Access, Digital Object Identifier 10.1109/Access.2021.3109216, date of publication Aug. 30, 2021, date of current version Sep. 9, 2021, pp. 1-22.

Hunter, Jenny, "Pioneering microscopic reality with new AI-powered microscopes", https://research.ibm.com/blog/microscopic-reality-ai-microscopes, Mar. 22, 2018, pp. 1-5.

IBM, "IBM Environmental Intelligence Suite", https://www.ibm. com/products/environmental-intelligence-suite, accessed Jan. 29, 2022, pp. 1-6.

Karl et al., "Metabolic balance of the open sea", https://www.nature. com/articles/426032a, Nature—vol. 426, Nov. 6, 2003, p. 1.

Khatib et al., "Learning the Physics of All-Dielectric Metamaterials with Deep Lorentz Neural Networks", Adv. Optical Mater. 2022, 2200097, https://onlinelibrary.wiley.com/doi/epdf/10.1002/adom. 202200097, 2022, pp. 1-10.

NASA, "Orbiting Carbon Observatory 2", https://www.nasa.gov/mission_pages/oco2/index.html, accessedNov. 29, 2022, pp. 1-3.

Pierrot et al., "Recommendations for autonomous underway pC02 measuring systems and data-reduction routines", Deep-Sea Research II 56 (2009), ReseachGate, https://www.researchgate.net/publication/223418367, Jan. 2009, pp. 1-12.

Ruch, Patrick, "Hypertaste: An AI-assisted e-tongue for fast and portable fingerprinting of complex liquids", Jul. 5, 2019, https://www.ibm.com/blogs/research/2019/07/hypertaste-ai-assisted-etongue/, pp. 1-9.

Takahashi et al., "Climatological mean and decadal change in surface ocean $pCO_2$, and net sea-air $CO_2$ flux over the global oceans", Deep-Sea Research II 56 (2009) 554-577, <https://www. sciencedirect.com/science/article/abs/pii/S0967064508004311>.

TNFD, "Developing and delivering a risk management and disclosure framework for organizations to report and act on evolving nature-related risks", Taskforce on Nature-related Financial Disclosures, http://tnfd.global/, accessed Nov. 29, 2022, pp. 1-8.

* cited by examiner

100

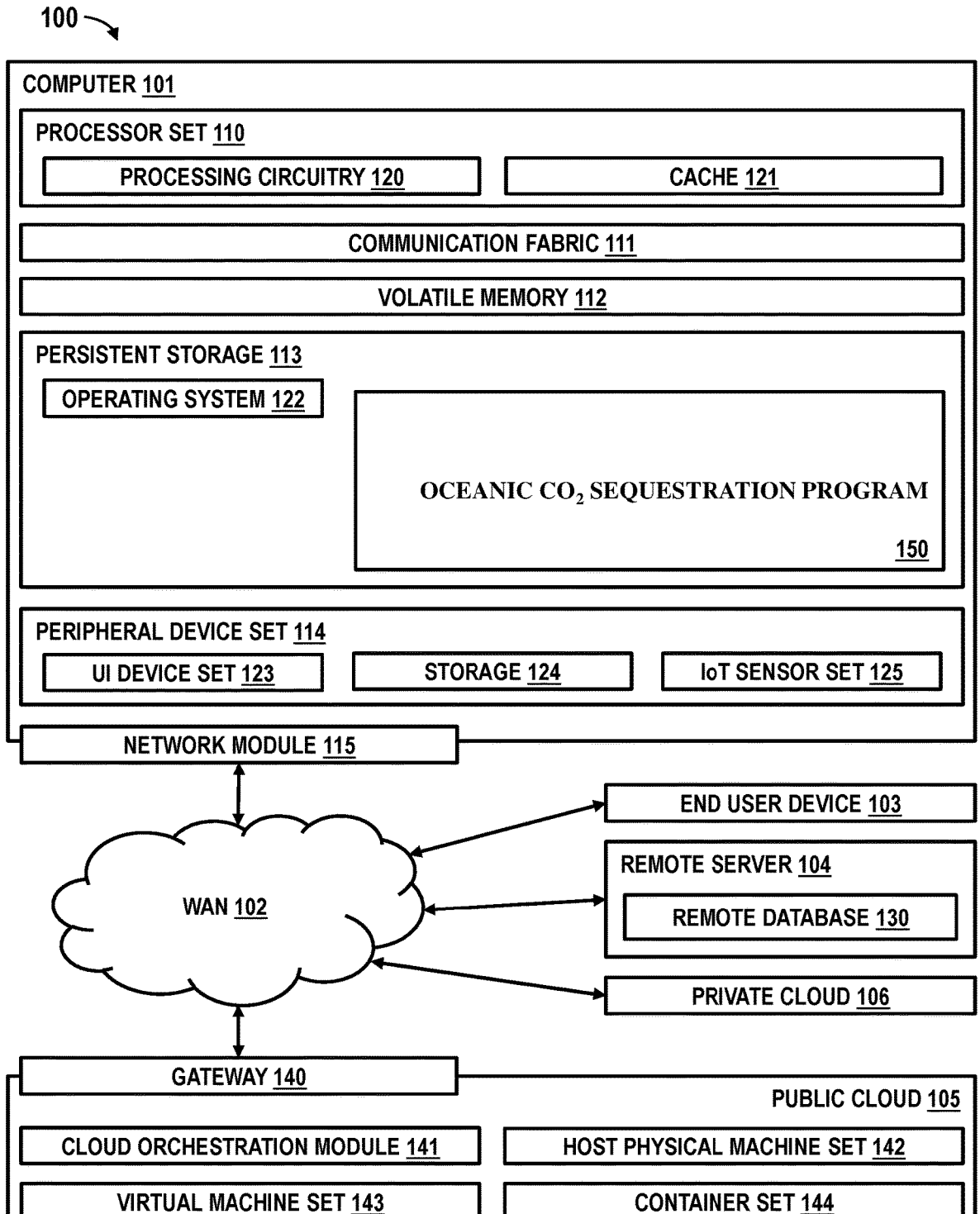

COMPUTER 101

PROCESSOR SET 110

PROCESSING CIRCUITRY 120          CACHE 121

COMMUNICATION FABRIC 111

VOLATILE MEMORY 112

PERSISTENT STORAGE 113

OPERATING SYSTEM 122

OCEANIC $CO_2$ SEQUESTRATION PROGRAM

150

PERIPHERAL DEVICE SET 114

UI DEVICE SET 123          STORAGE 124          IoT SENSOR SET 125

NETWORK MODULE 115

WAN 102

END USER DEVICE 103

REMOTE SERVER 104

REMOTE DATABASE 130

PRIVATE CLOUD 106

GATEWAY 140

PUBLIC CLOUD 105

CLOUD ORCHESTRATION MODULE 141          HOST PHYSICAL MACHINE SET 142

VIRTUAL MACHINE SET 143          CONTAINER SET 144

OBTAIN A PLURALITY OF
OCEANIC CARBON
MEASUREMENTS
202

OBTAIN CONTRIBUTORY
FEATURES TO VARIANCES OF
THE OBTAINED $CO_2$
MEASUREMENTS
204

MAP THE OBTAINED OCEANIC
$CO_2$ MEASUREMENTS TO THE
CONTRIBUTORY FEATURES TO
GENERATE AN A PRIORI OCEANIC
SPATIOTEMPORAL $CO_2$ MODEL

206

USE THE A PRIORI OCEANIC
SPATIOTEMPORAL $CO_2$ MODEL TO
GENERATE ESTIMATED $CO_2$
MEASUREMENTS
208

QUANTIFICATION OF OCEANIC CARBON DIOXIDE SEQUESTRATION

BACKGROUND

Exemplary embodiments of the present inventive concept relate to oceanic carbon sequestration, and more particularly, to quantification of oceanic carbon dioxide sequestration.

The global ocean, which is comprised of 5 ocean basins, is the largest net sink of atmospheric carbon dioxide ($CO_2$) in the world. The global ocean absorbs roughly 31% of all of the carbon dioxide released into the atmosphere. It is estimated that approximately 1.8 petagrams of carbon per year (Pg C year$^{-1}$) are sequestered by the global ocean from dissolved $CO_2$ sources, but the uncertainty as to the precise quantity is still very large (+/−~0.7 Pg C year$^{-1}$). The flux of oceanic $CO_2$ influences climate change rate, air pollution, and ocean acidification. When $CO_2$ dissolves in saltwater it can form carbonic acid, which can have a dire effect on ocean ecosystems.

However, the 5 ocean basins and regions thereof vary widely with respect to oceanic $CO_2$ absorption and emission. For example, the Equatorial Pacific predominantly releases $CO_2$ to the atmosphere, whereas the North Atlantic predominantly absorbs $CO_2$. In addition to variance among ocean basins and regions thereof, net oceanic $CO_2$ sequestration also varies with respect to other factors, such as time. Given how expansive the global ocean is, it is economically and practically infeasible to directly measure global oceanic $CO_2$ sequestration at every location simultaneously, let alone on a continuous basis. Thus, obtaining accurate measures of overall and spatiotemporal $CO_2$ sequestration is an unsolved dilemma.

SUMMARY

Exemplary embodiments of the present inventive concept relate to a method, a computer program product, and a system for quantifying oceanic $CO_2$ sequestration.

According to an exemplary embodiment of the present inventive concept, a method is provided for quantification of oceanic $CO_2$ sequestration. The method includes obtaining a plurality of oceanic spatiotemporal carbon dioxide (CO2) measurements. A plurality of spatiotemporal chlorophyll a (Chl-a) and a plurality of oceanic temperature measurements are obtained. The obtained plurality of oceanic spatiotemporal CO2 measurements is mapped to the obtained plurality of spatiotemporal Chl-a and the plurality of oceanic temperature measurements in a multidimensional grid. At least one a priori oceanic spatiotemporal CO2 estimate is generated based on the multidimensional grid.

According to an exemplary embodiment of the present inventive concept, a computer program product is provided for quantifying oceanic carbon dioxide ($CO_2$) sequestration. The computer program product includes one or more computer-readable storage media and program instructions stored on the one or more non-transitory computer-readable storage media capable of performing a method. The method includes obtaining a plurality of oceanic spatiotemporal carbon dioxide ($CO_2$) measurements. A plurality of spatiotemporal chlorophyll a (Chl-a) and a plurality of oceanic temperature measurements are obtained. The obtained plurality of oceanic spatiotemporal $CO_2$ measurements is mapped to the obtained plurality of spatiotemporal Chl-a and the plurality of oceanic temperature measurements in a multidimensional grid. At least one a priori oceanic spatiotemporal $CO_2$ estimate is generated based on the multidimensional grid.

According to an exemplary embodiment of the present inventive concept, a computer system is provided for quantifying oceanic carbon dioxide ($CO_2$) sequestration. The computer system includes one or more computer processors, one or more computer-readable storage media, and program instructions stored on the one or more of the computer-readable storage media for execution by at least one of the one or more processors capable of performing a method. The method includes obtaining a plurality of oceanic spatiotemporal carbon dioxide ($CO_2$) measurements. A plurality of spatiotemporal chlorophyll a (Chl-a) and a plurality of oceanic temperature measurements are obtained. The obtained plurality of oceanic spatiotemporal $CO_2$ measurements is mapped to the obtained plurality of spatiotemporal Chl-a and the plurality of oceanic temperature measurements in a multidimensional grid. At least one a priori oceanic spatiotemporal $CO_2$ estimate is generated based on the multidimensional grid.

BRIEF DESCRIPTION OF THE DRAWINGS

The following detailed description, given by way of example and not intended to limit the exemplary embodiments solely thereto, will best be appreciated in conjunction with the accompanying drawings, in which:

FIG. 1 illustrates a schematic diagram of computing environment 100, which may include the quantification of oceanic $CO_2$ sequestration program 150, in accordance with an exemplary embodiment of the present inventive concept.

Figure 2:
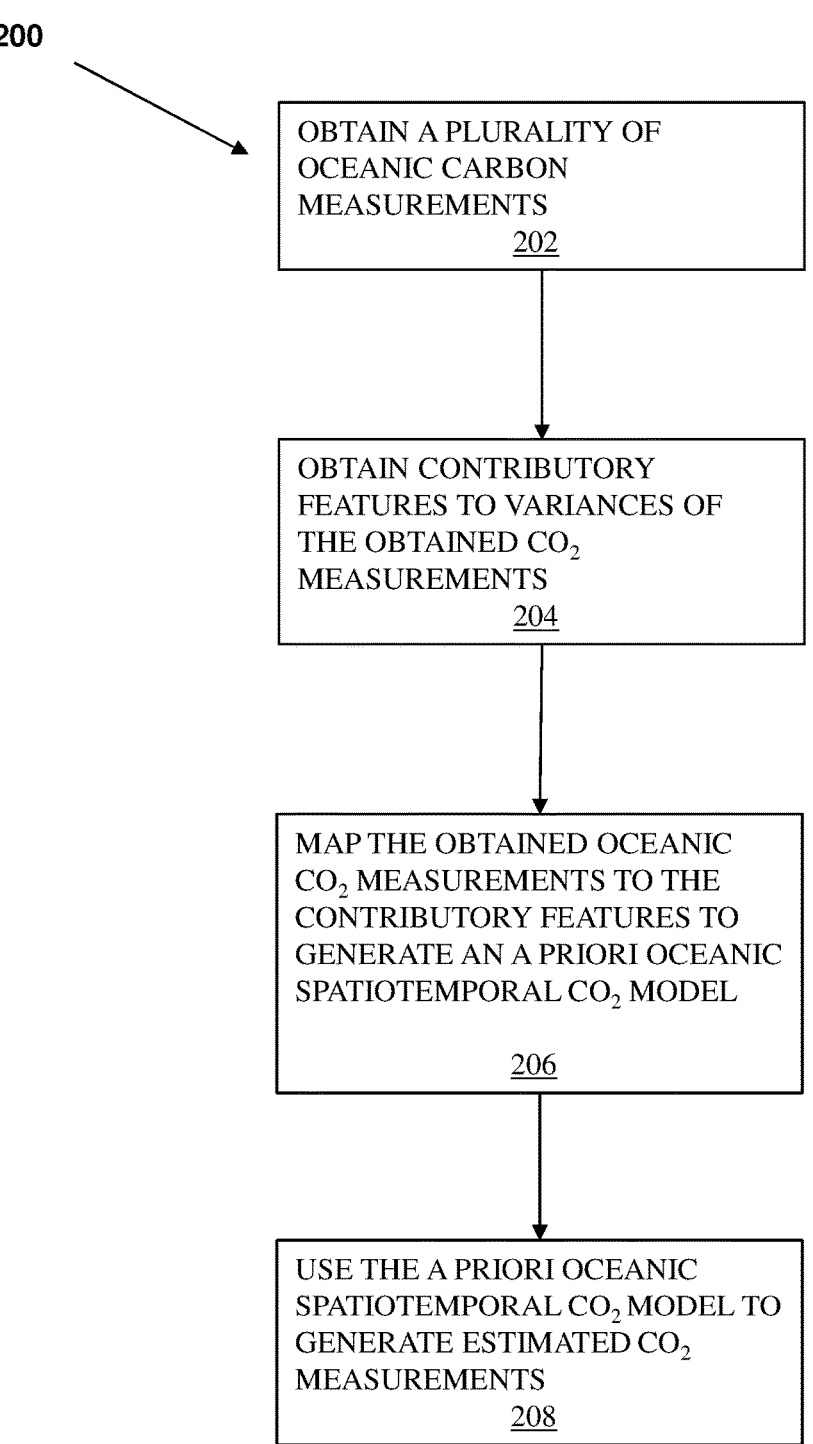
FIG. 2 illustrates a flowchart of quantification of oceanic $CO_2$ sequestration 200, in accordance with an exemplary embodiment of the present inventive concept.

It is to be understood that the included drawings are not necessarily drawn to scale/proportion. The included drawings are merely schematic examples to assist in understanding of the present inventive concept and are not intended to portray fixed parameters. In the drawings, like numbering may represent like elements.

DETAILED DESCRIPTION

Exemplary embodiments of the present inventive concept are disclosed hereafter. However, it shall be understood that the scope of the present inventive concept is dictated by the claims. The disclosed exemplary embodiments are merely illustrative of the claimed system, method, and computer program product. The present inventive concept may be embodied in many different forms and should not be construed as limited to only the exemplary embodiments set forth herein. Rather, these included exemplary embodiments are provided for completeness of disclosure and to facilitate an understanding to those skilled in the art. In the detailed description, discussion of well-known features and techniques may be omitted to avoid unnecessarily obscuring the presented exemplary embodiments.

References in the specification to "one embodiment," "an embodiment," "an exemplary embodiment," etc., indicate that the embodiment described may include a particular feature, structure, or characteristic, but not every embodiment may necessarily include that feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether explicitly described.

In the interest of not obscuring the presentation of the exemplary embodiments of the present inventive concept, in the following detailed description, some processing steps or operations that are known in the art may have been combined for presentation and for illustration purposes, and in some instances, may have not been described in detail. Additionally, some processing steps or operations that are known in the art may not be described at all. The following detailed description is focused on the distinctive features or elements of the present inventive concept according to various exemplary embodiments.

Accurate quantification of oceanic $CO_2$ sequestration across spatial and temporal domains can be critical to our understanding of anthropogenic impacts (e.g., climate change), informing associated policies, preserving the integrity of ocean ecosystems, and using carbon trading platforms, such as the VERRA Verified Carbon Standard. The present inventive concept provided herein can quantify oceanic $CO_2$ sequestration across a spatiotemporal domain based on interpolative modelling by mapping a plurality of empirical oceanic $CO_2$ measurements to a plurality of chlorophyll and/or oceanic temperature measurements. Thus, quantification of oceanic $CO_2$ sequestration can be subsequently estimated a priori without necessitating continuous and in situ measurements at a specific time and/or place. The present inventive concept can leverage sampled spatiotemporal variables, such as ocean surface temperature and/or Chl-a to estimate $CO_2$ values which cannot be meaningfully obtained using common sampling approaches. This is particularly true since accurate estimates of $CO_2$ fluxes need to consider volumetric concentrations that can include the ocean depth dimension.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Computing environment 100, as shown in FIG. 1, contains an example of an environment for the execution of at least some of the computer code involved in performing the inventive methods, such as a quantification of ocean $CO_2$ sequestration program 150. In addition to block 150, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and block 150, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip."

In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in block 150 in persistent storage 113.

COMMUNICATION FABRIC 111 is the signal conduction path that allows the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, volatile memory 112 is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid state storage devices. Operating system 122 may take several forms, such as various known proprietary operating systems or open source Portable Operating System Interface-type operating systems that employ a kernel. The code included in block 150 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN 102 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 103 is any computer system that is used and controlled by an end user (for example, a customer of an enterprise that operates computer 101) and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

REMOTE SERVER 104 is any computer system that serves at least some data and/or functionality to computer

101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

FIG. 2 illustrates a quantification of oceanic $CO_2$ sequestration flowchart 200, in accordance with an exemplary embodiment of the present inventive concept.

The quantification of oceanic $CO_2$ sequestration program 150 can obtain a plurality of oceanic carbon measurements (step 202). The plurality of oceanic carbon measurements can include $CO_2$ measurements. However, the present inventive concept is not limited thereto. For example, the plurality of carbon measurements can also include carbon by-products relevant to $CO_2$ dissolution. The $CO_2$ measurements can include a $CO_2$ partial pressure ($pCO_2$). The plurality of oceanic $CO_2$ measurements can also be labelled with a time (e.g., clock time, second, minute, hour, day, month, season, year, etc.) and a location (e.g., global positioning coordinates (GPS) (e.g., longitude, latitude), depth, ocean layer, ocean basin, grid unit, predefined area, etc.) for one or more measurements (i.e., oceanic spatiotemporal $CO_2$ measurements). The oceanic $CO_2$ measurements can be transmitted by at least one user (e.g., crowdsourcing) and/or at least one autonomous vessel (e.g., Mayflower Autonomous Ship (MAS)) at a plurality of times and/or locations. The plurality of oceanic $CO_2$ measurements can include oceanic $CO_2$ measurements measured at a substantially same location (e.g., within a predetermined threshold physical/grid unit distance), but at different times. The quantification of oceanic $CO_2$ sequestration program 150 can identify variances in oceanic $CO_2$ measurements that exceed a predetermined historic/predicted threshold.

The quantification of oceanic $CO_2$ sequestration program 150 can coordinate the frequency, time, and/or location in which the oceanic $CO_2$ measurements are taken, such as by the at least one autonomous vessel (e.g., selecting a GPS route/destination(s), schedule measurement times/intervals/frequencies, set ocean layer(s) and/or measurement depth(s), etc.). The quantification of oceanic $CO_2$ sequestration program 150 can obtain a global map and/or a topographical map (e.g., includes the global ocean floor terrain and depth) from a user or via a network and perform AI analysis. The quantification of oceanic $CO_2$ sequestration program 150 can set routes that avoid land masses and water that is below a predetermined depth. The quantification of oceanic $CO_2$ sequestration program 150 can obtain/analyse data related to past/present/future weather and/or ship routes in selecting a GPS route to avoid hazard and/or make dynamic route changes accordingly. The quantification of oceanic $CO_2$ sequestration program 150 can sample oceanic $CO_2$ measurements from a plurality of ocean layers and/or depths for a same location and/or at a substantially same time. The quantification of oceanic $CO_2$ sequestration program 150 can obtain oceanic $CO_2$ measurements with greater relative frequency in locations with identified variances that exceed a predetermined threshold and/or lack of historic data. The increased frequency of oceanic $CO_2$ measurements can be proportionate to the degree of identified variance and/or historic data deficiency at a location.

The at least one autonomous vessel can be equipped with an AI-backed sensor which can measure the composition of liquids (e.g., molecules, compounds, elements, ions, etc.), such as Hypertaste. In the case of a plurality of autonomous vessels, the quantification of oceanic $CO_2$ sequestration program 150 can coordinate routes. For example, a pair of autonomous vessels can coordinate opposite routes with respect to origin and destination. The quantification of oceanic $CO_2$ sequestration program 150 can generate and/or populate a digitized global map with the plurality of oceanic $CO_2$ measurements and associated information (e.g., identified variances; demarcated ocean basins and regions thereof; ocean front detection; averaged and/or time-adjusted concentration heatmaps; time, location, measurement annotations; etc.). The digitized global map can also include a grid array comprised of grid units of a predetermined size(s).

For example, the quantification of oceanic $CO_2$ sequestration program 150 deploys a MAS equipped with Hypertaste to obtain oceanic spatiotemporal $pCO_2$ measurements. The quantification of oceanic $CO_2$ sequestration program 150 designates a MAS route which traverses each of the 5 ocean basins while avoiding times and locations that risk encountering hurricanes and ship traffic. En route, the MAS obtains periodic oceanic spatiotemporal $pCO_2$ measurements within the euphotic zone (i.e., 0-100 meters (m) in depth) in addition to the corresponding latitudes, longitudes, times, and precise measurement depths. The MAS measures the oceanic spatiotemporal $pCO_2$ measurements with increased frequency in the North Atlantic Ocean, which is identified to exhibit greater variance. Specific regions of high primary productivity, such as coral reefs, seagrass forests, and kelp farms are sampled at higher frequencies. The quantification of oceanic $CO_2$ sequestration program 150 incorporates the spatiotemporal $pCO_2$ measurements onto a digitized global map for user visualization, which includes a heatmap and obtained measurement annotations.

The quantification of oceanic $CO_2$ sequestration program 150 can obtain contributory features to variances of the obtained $CO_2$ measurements (step 204). The contributory features can include spatiotemporal Chlorophyll-a (Chl-a) and spatiotemporal surface temperature (SST) measurements for at least one location. The at least one location of the spatiotemporal Chl-a and SST measurements can include the location in which the oceanic $CO_2$ measurements are taken. The quantification of oceanic $CO_2$ sequestration program 150 can obtain the spatiotemporal Chl-a and SST measurements via satellite imaging and AI analysis. However, embodiments of the present inventive concept are not limited thereto. For example, the spatiotemporal Chl-a and/or SST measurements can also be obtained by the same or different at least one user and/or the same or different at least one autonomous vessel which can transmit the obtained oceanic $CO_2$ measurements. The quantification of oceanic $CO_2$ sequestration program 150 can obtain the contributory features contemporaneously and/or within a predetermined time and/or distance (e.g., meters, feet, miles, grid units, linear, square, custom, and/or circumferential, user selected bounded areas, etc.) of the obtained oceanic $CO_2$ measurements (e.g., automatically, randomly, at predetermined intervals of time (e.g., seconds, minutes, hours, days, weeks, months, user selected times, etc.), upon identifying a variance, etc.).

In an embodiment of the present inventive concept, the quantification of oceanic $CO_2$ sequestration program 150 can obtain additional contributory features for the at least one location. The additional contributory features may include, but are not limited to, past/present/future weather (e.g., UV index, wind speed and/or direction, temperature, attenuation of downwelling irradiance, cloud coverage, ambient air pressure, air quality and compositions thereof, etc.), additional ocean variable measurements (e.g., salinity, currents, ocean water composition, dissolved oxygen, mixing layer depth, layers and densities, temperature, vertical mixing velocity, horizontal velocity, acidity, tide, etc.), adjacent land carbon emission changes, moon phase, etc. Data related to the additional contributory features can be obtained via a network (e.g., streamed, keyword searched, etc.) and/or by the same or different at least one user and/or the same or different at least one autonomous vessel from the obtained oceanic $CO_2$ measurements and/or the obtained Chl-a and/or SST measurements. The quantification of oceanic $CO_2$ sequestration program 150 can use AI (e.g., data mining, natural language processing (NLP)) to extract the contributory features from the obtained data. The quantification of oceanic $CO_2$ sequestration program 150 can incorporate the contributory features, measurements, and annotations therefor into the digitized map.

For example, upon obtaining the oceanic spatiotemporal $pCO_2$ measurements, the quantification of oceanic $CO_2$ sequestration program 150 obtains satellite imaging at the substantially same time in a circumference of 100 miles from the location of the obtained oceanic spatiotemporal $pCO_2$ measurements in the North Atlantic Ocean. The quantification of oceanic $CO_2$ sequestration program 150 analyses the satellite imaging for measurements of the Chl-a and SST, and other pertinent remotely-sensed ocean variables. The quantification of oceanic $CO_2$ sequestration program 150 also obtains the ocean vertical mixing velocity, ocean horizontal velocity, and ocean acidity from the MAS, and adjacent land carbon emission changes via the network. The quantification of oceanic $CO_2$ sequestration program 150 incorporates the spatiotemporal Chl-a and SST measurements and additional contributory features on the digitized global map for the user visualization, which includes the heatmap and the measurement annotations.

The quantification of oceanic $CO_2$ sequestration program 150 can map the obtained oceanic $CO_2$ measurements to the contributory features to generate an a priori oceanic spatiotemporal $CO_2$ model (step 206). Geospatial variations can be informed by satellite surface measurements of Chl-a and SST. A relationship between Chl-a, temperature and $pCO_2$ can exist in the form: $pCO_2 = A.$ Chl$-a + B.SST + C$ with the coefficients A, B and C being functions of space and time. However, the regression coefficients can exhibit considerable spatiotemporal variability, which makes parametrising a priori estimates difficult. A machine learning model (e.g., convolutional neural network (CNN), CNN+(long short-term memory (LSTM), random forest, multilayer perceptron (MLP), etc.) can be trained to map the plurality of contributory features (e.g., Chl-a and SST measurements) to the plurality of oceanic $CO_2$ (e.g., $pCO_2$) measurements on a multidimensional grid (e.g., features=Chl-a+SST etc., labels=$pCO_2$). The spatiotemporal properties of the a priori oceanic spatiotemporal $CO_2$ model can be based on the multidimensional grid, which can be used to estimate $CO_2$ at locations and/or times for which there is no or limited real-time observation data (e.g., unmonitored or sparsely monitored locations). The availability of multidimensional (e.g., four-dimensional) measurements of $CO_2$ can provide a robust AI model estimate of oceanic spatiotemporal $CO_2$ values. This multidimensional measurement can be significantly enhanced by the AI-backed adaptive sampling approach to ensure measurements provide maximum uplift to model estimates. The a priori oceanic spatiotemporal $CO_2$ model can become more efficient as more data is provided, and consequently, the adaptive sampling approach can recommend reduced sampling at certain times and/or locations the longer the model is deployed.

For example, the quantification of oceanic $CO_2$ sequestration program 150 uses a CNN to map the MAS obtained oceanic spatiotemporal $pCO_2$ measurements to the corresponding contributory features, such as the spatiotemporal SST and Chl-a measurements in a multidimensional grid. The quantification of oceanic $CO_2$ sequestration program 150 uses the multidimensional grid to generate an a priori oceanic spatiotemporal $CO_2$ model.

The quantification of oceanic $CO_2$ sequestration program 150 can use the a priori oceanic spatiotemporal $CO_2$ model to generate estimated $CO_2$ measurements (step 208). The a priori oceanic spatiotemporal $CO_2$ model can update the digitized global map to synchronize with real-time a priori oceanic spatiotemporal $CO_2$ estimates and/or estimated contributory features. The user can also input at least one of time, location, and/or contributory features to the quantification of oceanic $CO_2$ sequestration program 150, which can output associated a priori oceanic spatiotemporal $CO_2$ estimates. When a time span(s) is input, the quantification of oceanic $CO_2$ sequestration program 150 can depict or describe the progressive changes in a priori oceanic spatiotemporal $CO_2$ estimates (e.g., at predetermined intervals, overall, etc.) and contributory features. Newly obtained spatiotemporal SST and Chl-a measurements can be input to the a priori oceanic spatiotemporal $CO_2$ model, and the oceanic $CO_2$ sequestration program 150 can generate a priori oceanic spatiotemporal $CO_2$ estimates based thereon. The oceanic $CO_2$ sequestration program 150 can compare the estimated spatiotemporal Chl-a and/or SST measurements and adjust the model accordingly. Similarly, newly obtained oceanic spatiotemporal $CO_2$ measurements can be input to the a priori oceanic spatiotemporal $CO_2$ model, and the oceanic $CO_2$ sequestration program 150 can evaluate the estimation accuracy and adjust the model accordingly.

A data management module can extract spatiotemporal $CO_2$ measurement estimates therefor and store them in a standardized, quality-checked, international formatted repository. Concepts from transfer learning can be used to adapt the deployed oceanic spatiotemporal $CO_2$ model for one location to a new location, thereby reducing the volumes of data that must be collected for the new location. Once trained, the a priori oceanic spatiotemporal $CO_2$ model can be deployed to estimate $CO_2$ ($pCO_2$) at any location from the provided features (satellite surface estimates with optional marine model and weather data). Transformers or foundation models can be deployed to improve transferability and scalability of models. The ML model can be further constrained by known physical relationships such as, but not limited to, density and/or partial differential equations. In an embodiment of the present inventive concept, an uncertainty quantification module can compute confidence bounds for the generated oceanic spatiotemporal $CO_2$ measurement estimates and/or contributory features.

For example, at the request of a user, the quantification of oceanic $CO_2$ sequestration program 150 obtains and analyses satellite imaging of Chl-a and SST measurements in the North Atlantic Ocean for several sampling points in April (a month in which icebergs are plentiful, making direct measurement tedious, dangerous, and impracticable). The quantification of oceanic $CO_2$ sequestration program 150 provides a priori oceanic spatiotemporal $CO_2$ estimates for the North Atlantic Ocean that correspond to the month of April with a confidence measure of 75% to 83%. In contrast, the quantification of oceanic $CO_2$ sequestration program 150 generates a priori oceanic spatiotemporal $CO_2$ estimates for the South Atlantic Ocean (a relatively lower variance area) in April with a confidence measure of 85% to 93% without necessitating satellite imaging given abundant prior training.

Based on the foregoing, a computer system, method, and computer program product have been disclosed. However, numerous modifications, additions, and substitutions can be made without deviating from the scope of the exemplary embodiments of the present inventive concept. Therefore, the exemplary embodiments of the present inventive concept have been disclosed by way of example and not by limitation.

The invention claimed is:

1. A method for quantifying oceanic carbon dioxide ($CO_2$) sequestration, the method comprising:

obtaining a plurality of oceanic spatiotemporal carbon dioxide ($CO_2$) measurements using a plurality of $CO_2$ sensors;

obtaining a plurality of spatiotemporal chlorophyll a (Chl-a) and a plurality of oceanic temperature measurements using a plurality of spatiotemporal sensors;

training a machine learning model to map the plurality of oceanic spatiotemporal $CO_2$ measurements to the plurality of spatiotemporal Chl-a and the plurality of oceanic temperature measurements in a multidimensional grid;

generating at least one a priori oceanic spatiotemporal $CO_2$ estimate based on the multidimensional grid, improving accuracy and spatial resolution of locating $CO_2$ sequestration;

outputting the at least one priori oceanic spatiotemporal $CO_2$ estimate to a carbon monitoring system for use in climate and environmental policy modeling; and coordinating movements of an autonomous vessel to obtain measurements in ocean locations identified by the climate and environmental policy modeling as increasing the accuracy and spatial resolution of locating $CO_2$ sequestration.

2. The method of claim 1, wherein the at least one a priori oceanic spatiotemporal $CO_2$ estimate is generated based on a provided spatiotemporal Chl-a measurement and a provided oceanic surface temperature (SST) measurement.

3. The method of claim 2, wherein the obtained plurality of oceanic spatiotemporal $CO_2$ measurements and the generated at least one a priori oceanic spatiotemporal $CO_2$ estimate are measured in partial pressures of $CO_2$ ($pCO_2$).

4. The method of claim 3, wherein at least some of the obtained plurality of oceanic spatiotemporal $pCO_2$ measurements are obtained by the autonomous vessel using Hypertaste.

5. The method of claim 4, wherein the obtaining the plurality of spatiotemporal Chl-a and oceanic temperature measurements is performed using satellite imaging within a predetermined time and a predetermined distance of the obtained plurality of oceanic spatiotemporal $pCO_2$ measurements.

6. The method of claim 5, further comprising:

identifying ocean locations with spatiotemporal $pCO_2$ measurement variances that exceed a predetermined threshold.

7. A computer program product for quantifying oceanic carbon dioxide ($CO_2$) sequestration, the computer program product comprising:

one or more computer-readable storage media; and program instructions stored on the one or more computer-readable storage media to perform operations comprising:

obtaining a plurality of oceanic spatiotemporal carbon dioxide ($CO_2$) measurements using a plurality of $CO_2$ sensors;

obtaining a plurality of spatiotemporal chlorophyll a (Chl-a) and a plurality of oceanic temperature measurements using a plurality of spatiotemporal sensors;

training a machine learning model to map the plurality of oceanic spatiotemporal $CO_2$ measurements to the plurality of spatiotemporal Chl-a and the plurality of oceanic temperature measurements in a multidimensional grid;

generating at least one a priori oceanic spatiotemporal $CO_2$ estimate based on the multidimensional grid, improving accuracy and spatial resolution of locating $CO_2$ sequestration;

outputting the at least one priori oceanic spatiotemporal $CO_2$ estimate to a carbon monitoring system for use in climate and environmental policy modeling; and coordinating movements of an autonomous vessel to obtain measurements in ocean locations identified by the climate and environmental policy modeling as increasing the accuracy and spatial resolution of locating $CO_2$ sequestration.

8. The computer program product of claim 7, further comprising:

generating an a priori oceanic $CO_2$ estimate model using the multidimensional grid.

9. The computer program product of claim 8, wherein the at least one a priori oceanic spatiotemporal $CO_2$ measurement is generated based on a provided spatiotemporal Chl-a measurement and a provided oceanic surface temperature (SST) measurement.

10. The computer program product of claim 9, wherein the obtained plurality of oceanic spatiotemporal $CO_2$ measurements and the generated at least one a priori oceanic spatiotemporal $CO_2$ estimate are measured in partial pressures of $CO_2$ ($pCO_2$).

11. The computer program product of claim 10, wherein at least some of the obtained plurality of oceanic spatiotemporal $pCO_2$ measurements are obtained by an autonomous vessel using Hypertaste.

12. The computer program product of claim 11, wherein the obtaining the plurality of spatiotemporal Chl-a and oceanic temperature measurements is performed using satellite imaging within a predetermined time and a predetermined distance of the obtained plurality of oceanic spatiotemporal $pCO_2$ measurements.

13. The computer program product of claim 12, further comprising:

identifying ocean locations with spatiotemporal $pCO_2$ measurement variances that exceed a predetermined threshold; and coordinating the autonomous vessel to measure more frequently in the identified ocean locations with the spatiotemporal $pCO_2$ measurement variances that exceed the predetermined threshold.

14. A computer system for quantifying oceanic carbon dioxide ($CO_2$) sequestration, the computer system comprising:

one or more computer processors, one or more computer-readable storage media, and program instructions stored on the one or more of the computer-readable storage media for execution by at least one of the one or more processors capable of performing a method, the method comprising:

obtaining a plurality of oceanic spatiotemporal carbon dioxide ($CO_2$) measurements using a plurality of $CO_2$ sensors;

obtaining a plurality of spatiotemporal chlorophyll a (Chl-a) and a plurality of oceanic temperature measurements using a plurality of spatiotemporal sensors;

training a machine learning model to map the plurality of oceanic spatiotemporal $CO_2$ measurements to the plurality of spatiotemporal Chl-a and the plurality of oceanic temperature measurements in a multidimensional grid;

generating at least one a priori oceanic spatiotemporal $CO_2$ estimate based on the multidimensional grid, improving accuracy and spatial resolution of locating $CO_2$ sequestration;

outputting the at least one priori oceanic spatiotemporal $CO_2$ estimate to a carbon monitoring system for use in climate and environmental policy modeling; and coordinating movements of an autonomous vessel to obtain measurements in ocean locations identified by the climate and environmental policy modeling as increasing the accuracy and spatial resolution of locating $CO_2$ sequestration.

15. The computer system of claim 14, wherein the at least one a priori oceanic spatiotemporal $CO_2$ estimate is generated based on a provided spatiotemporal Chl-a measurement and a provided oceanic surface temperature (SST) measurement.

16. The computer system of claim 15, wherein the obtained plurality of oceanic spatiotemporal $CO_2$ measurements and the generated at least one a priori oceanic spatiotemporal $CO_2$ estimate are measured in partial pressures of $CO_2$ ($pCO_2$).

17. The computer system of claim 16, wherein at least some of the obtained plurality of oceanic spatiotemporal $pCO_2$ measurements are obtained by autonomous vessel using Hypertaste.

18. The computer system of claim 17, wherein the obtaining the plurality of spatiotemporal Chl-a and oceanic temperature measurements is performed using satellite imaging within a predetermined time and a predetermined distance of the obtained plurality of oceanic spatiotemporal $pCO_2$ measurements.

\* \* \* \* \*